United States Patent
Magnet et al.

(10) Patent No.: US 9,078,837 B2
(45) Date of Patent: *Jul. 14, 2015

(54) FILAMENTOUS POLYMER PARTICLES AND USE THEREOF AS RHEOLOGY MODIFIERS

(75) Inventors: Stephanie Magnet, Morlanne (FR); Raber Inoubli, Pau (FR); Laurence Couvreur, Paris (FR); Bernadette Charleux, Lyons (FR); Segolene Brusseau, Cachan (FR)

(73) Assignees: Arkema France (FR); Universite Pierre et Marie Curie, Centre National De La Recherche Scientifique (FR); Universite Claude Bernard Lyon (FR); Ecole Superieure de Chimie Physique Electronique de Lyon (FR)

( * ) Notice: Subject to any disclaimer, the term of this patent is extended or adjusted under 35 U.S.C. 154(b) by 26 days.

This patent is subject to a terminal disclaimer.

(21) Appl. No.: 13/996,766
(22) PCT Filed: Dec. 22, 2011
(86) PCT No.: PCT/FR2011/053145
§ 371 (c)(1),
(2), (4) Date: Aug. 26, 2013
(87) PCT Pub. No.: WO2012/085473
PCT Pub. Date: Jun. 28, 2012

(65) Prior Publication Data
US 2014/0039067 A1 Feb. 6, 2014

(30) Foreign Application Priority Data
Dec. 23, 2010 (FR) .................... 10 61191

(51) Int. Cl.
A61K 8/90 (2006.01)
C08F 2/22 (2006.01)
(Continued)

(52) U.S. Cl.
CPC ... A61K 8/90 (2013.01); C08F 2/22 (2013.01); C08F 2/38 (2013.01); C08F 293/005 (2013.01);
(Continued)

(58) Field of Classification Search
CPC ............... A61K 8/90; C08F 2/22; C08F 2/38; C08F 293/005; C09D 153/00; C09K 8/588; C09K 2208/08; D01F 6/36; D01F 6/42; E21B 43/16; Y10T 428/298
USPC .......... 424/401, 78.8; 524/460; 526/193, 318, 526/319
See application file for complete search history.

(56) References Cited

U.S. PATENT DOCUMENTS 4,563,290 A  1/1986 Okada et al.
4,584,358 A  4/1986 McCormick et al.
(Continued)

OTHER PUBLICATIONS

Delaittre, G et al "Aqueous Suspension of Amphiphilie Diblock Copolymer Nanoparticles Prepared in situ from a Water-soluble poly(sodium acrylate) alkoxyamine macroinitiator" Soft Matter R Soc ChemUK vol. 2, No. 3, Mar. 7, 2006 pp. 223-231.

*Primary Examiner* — Jane C Osweeki
(74) *Attorney, Agent, or Firm* — Thomas F. Roland (57) ABSTRACT

The invention relates to polymer particles in the form of filaments formed by block copolymers, as well as to the use thereof as rheology modifiers for aqueous or organic solutions. A first aspect of the invention relates to filamentous polymer particles having a length/diameter ratio greater than 100, said particles being formed by block copolymers synthesized by controlled radical emulsion polymerization in emulsion, performed using at least one hydrophobic monomer in the presence of a water-soluble marcoinitiator. The invention is characterized in that the filamentous particles are obtained in an aqueous medium for the synthesis of said block copolymers, performed by heating the reaction medium to a temperature of 60 to 120° C., the final block copolymer containing between 10 and 50 mol. % of the water-soluble macroinitiator and the hydrophobic monomer conversion rate being at least 50%. A second aspect of the invention relates to a method for modifying the rheology of an organic or aqueous solution using said filamentous polymer particle.

15 Claims, 5 Drawing Sheets (51) Int. Cl.
  C08F 2/38      (2006.01)
  C08F 293/00    (2006.01)
  C09K 8/588     (2006.01)
  D01F 6/36      (2006.01)
  D01F 6/42      (2006.01)
  C09D 153/00    (2006.01)
  E21B 43/16     (2006.01)

(52) U.S. Cl.
  CPC .............. *C09D 153/00* (2013.01); *C09K 8/588* (2013.01); *D01F 6/36* (2013.01); *D01F 6/42* (2013.01); *E21B 43/16* (2013.01); *C09K 2208/08* (2013.01); *Y10T 428/298* (2015.01)

(56) References Cited

U.S. PATENT DOCUMENTS

| | | | |
|---|---|---|---|
| 8,481,631 B2 * | 7/2013 | Dire et al. | 524/460 |
| 2008/0045420 A1 * | 2/2008 | Karagianni et al. | 507/121 |
| 2011/0166282 A1 | 7/2011 | Dire et al. | |
| 2013/0338315 A1 * | 12/2013 | Magnet et al. | 525/299 |

* cited by examiner

FILAMENTOUS POLYMER PARTICLES AND USE THEREOF AS RHEOLOGY MODIFIERS

This application claims benefit, under U.S.C. §119 or §365 of PCT Application Number PCT/FR2011/053145, filed Dec. 22, 2011, and French Patent Application Number FR 10.61191, filed Dec. 23, 2010.

FIELD OF THE INVENTION

The present invention pertains to polymer particles in filament form in that are composed of block copolymers, and to their use as rheology modifiers for aqueous or organic solutions.

BACKGROUND OF THE INVENTION

When a natural gas or oil deposit reaches the end of its normal lifetime, the major part of the hydrocarbons (up to two thirds) remains in the ground, since they are too difficult or too expensive to extract. It is estimated that recovery of just 1% more throughout the world would be equivalent to 20-30 billion extra barrels of oil.

Techniques of assisted hydrocarbon (oil and natural gas) recovery by chemical means involve injecting an aqueous phase into the underground reservoir via injecting wells, which are situated at a distance from the producing wells. The injected aqueous phase maintains the pressure in the reservoir and displaces the hydrocarbons toward the production wells. The aim is also to increase the fluidity of the oil to be recovered, or to reduce the permeability of certain subsoil strata whose characteristics are detrimental to effective scavenging of the reservoir.

The efficacy of these methods is limited by the difference in viscosity between oil and water, which causes the water to seek to pass directly from the injection well to the production well.

The aqueous phase for injection into a well is usually admixed with chemical products whose role is to increase its viscosity, allowing more effective scavenging of the deposit as a whole. The increase in viscosity is manifested in a reduction in the mobility ratio between the aqueous phase and the hydrocarbon phase.

The skilled person is aware that an increase in the viscosity of an aqueous solution with very low levels of additive can be obtained through the use of water-soluble polymers which have a very high molar mass and/or possess monomer units which are charged (in particular by acid groups), or through the use of hydrophilic biopolymers which give rigid structures.

Charged water-soluble polymers (such as HPMAs or high molecular weight polyacrylamides, which are acrylamides copolymerized with an ionic monomer) have a viscosifying character by substantially increasing the radius of gyration of the molecule, by virtue of the repulsive interactions of the charges present in the molecule. The presence of salts or a change in pH in the medium may "mask" these charges and suppress these interactions, and thereby suppress the viscosifying effect.

Hydrophilic biopolymers such as scleroglucan are very effective rheology modifiers, but have a great sensitivity to bacterial degradation. These molecules are "cut" by certain microorganisms, and thus loose any viscosifying and shear-thinning properties.

Other polymeric compounds have been used as rheology modifiers, examples being hydrophobically associative polymers (HAPs), which have a hydrophilic backbone and, along the chains, comprise small amounts of hydrophobic monomers which are able to combine in water in the form of hydrophobic nanodomains. These nanodomains act as points of temporary crosslinking and endow the HAPs with a marked shear-thinning character.

SUMMARY OF THE INVENTION

The aim of the present invention is to provide new polymeric compounds capable of modifying the rheology of aqueous or organic solutions, and overcoming the disadvantages set out above.

A first objective of the present invention is to provide polymeric structures capable, in a very low proportion, of modifying the rheology of the water injected into the well during tertiary hydrocarbon recovery, Another objective of the invention is to provide filamentous polymeric structures which are capable of retaining their morphology following substantial dilution in water and/or in an organic solvent. It has now been found that polymer particles in filament form composed of block copolymers have a viscosifying and shear-thinning character in dispersed medium, and do so at a very low concentration; furthermore, the viscosifying and shear-thinning effect of the filamentous particles according to the invention is unaffected by the presence of salt or by variations in pH of the medium, and said particles are not sensitive to bacterial degradation.

The invention, according to a first aspect, provides filamentous polymer particles composed of block copolymers synthesized by controlled radical emulsion polymerization. Characteristically these polymer particles take the form of cylinders having a length/diameter ratio of more than 100.

According to a first variant, said particles are synthesized from at least one hydrophobic monomer in the presence of a living macroinitiator derived from a nitroxide, characterized in that:
said filamentous particles are obtained in aqueous medium in a single step directly during the synthesis of said block copolymers, formed by heating the reaction medium at a temperature of 60 to 120° C.,
said macroinitiator is water-soluble,
the percentage of the molar mass of the water-soluble macroinitiator in the final block copolymer is between 10% and 50%, and in that
the degree of conversion of the hydrophobic monomer is at least 50%.

This direct technique for preparing filamentous particles does not require the use of organic cosolvent.

In the context of the present invention, the term "filamentous particles" corresponds to assemblies of amphiphilic macromolecules which, when in suspension in water (in other words, when they form an aqueous dispersion), take the form of filaments (in other words, flexible, solid cylinders) with a core composed of the hydrophobic elements and a surface composed of the hydrophilic elements of said macromolecules. These filamentous particles can be observed under a transmission electron microscope (TEM). The microscopy images show filaments with a diameter of greater than or equal to 5 nm and a length of more than 500 nm, preferably more than 1 micron, advantageously more than 5 microns. According to one embodiment, the length of the filamentous particles according to the invention is at least 10 micrometers.

In contradistinction to the filamentous particles, the spherical particles (or micelles) in suspension in water are assemblies of amphiphilic molecules which take the form of a solid sphere with a core composed of the hydrophobic elements of the molecules, and a surface composed of the hydrophilic elements.

Figure 1:
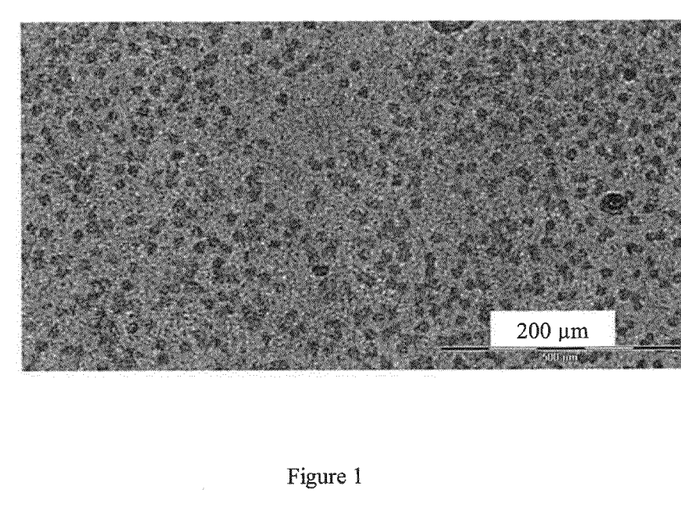
FIG. 1 is the image obtained by TEM for the spherical particles of comparative example 2, corresponding to the invention described in document WO 2009150367; the degree of conversion by mass is 67.2%, and the mass fraction of the hydrophilic moiety constituting the block copolymer (or "proportion of hydrophilic fraction") is 23.4% by weight.

In document WO 2009150367 the applicant had already described the preparation of polymer particles from at least one hydrophobic methacrylate monomer and another hydrophobic monomer in the presence of a living nitroxide macroinitiator derived from SG1. The polymer particles thus obtained take the form of spherical micelles, irrespective of the degree of conversion. They are characterized in comparative example 2 of the present invention and also in appended FIG. 1.

Surprisingly, it has now been found that in the presence of a water-soluble macroinitiator, and with selection of a specific ratio between the molar masses of the water-soluble macroinitiator and of the second, hydrophobic block, filamentous particles are obtained.

According to a second variant, said filamentous particles are synthesized by radical polymerization by reversible addition fragmentation transfer (RAFT) in water in the presence of a macromolecular RAFT agent (or RAFT macroagent) which is hydrophilic.

The filamentous particles according to the invention are advantageously not in thermodynamic equilibrium (they are said to be in a frozen state), in contrast to the wormlike micelles described above, which, under the effect of the dilution, enter the state of spherical micelles, which is a more thermodynamically stable state. This nonequilibrium thermodynamic state is independent of the glass transition value of the polymer, but is partly dependent on the length of the hydrophobic block. The form and structure of the filamentous particles according to the invention are maintained in dispersed medium, independently of their concentration in the medium, of the dialysis of the particles (FIG. 7), of the centrifuging of the medium (FIG. 8), and of variations in its pH (FIG. 9) or its salinity (FIG. 10).

According to a second aspect, the invention pertains to a method for modifying the rheology of an aqueous or organic solution by means of said filamentous polymer particles. This method comprises a step of adding these filamentous particles to an aqueous or organic solution in a mass fraction of from 100 to 10 000 ppm.

According to a further aspect, the invention is directed to a method for enhanced hydrocarbon extraction by means of a polymeric additive, wherein said additive is mixed with water or brine in a proportion of at least 500 ppm of additive and then this mixture is injected under pressure into the rock; characteristically, said additive consists of the filamentous polymer particles according to the invention.

According to a yet further aspect, the invention relates to a composition for modifying the rheology of an aqueous or organic solution, said composition comprising the filamentous polymer particles described above.

BRIEF DESCRIPTION OF THE DRAWINGS

The invention and the advantages it provides will be appreciated more fully in the light of the detailed description which follows, and of the appended figures, in which.

DETAILED DESCRIPTION OF THE INVENTION

The subject-matter of the present invention relates to the rheological properties (shear-viscosifying and shear-thinning character) in dispersed medium of copolymer particles having a very specific elongated fibril shape. it has now been found that, surprisingly, certain polymer particles have the property of increasing the viscosity of aqueous (or organic) solutions and, in so doing, of giving them a shear-thinning character.

The viscosifying character at very low concentration is provided by a pseudopercolation of the structure in dispersed medium that is obtained at very low concentrations. The shear-thinning character is obtained by a pseudodisentanglement obtained very rapidly (depending on the deformation gradient or shear rate) by virtue of the rigidity and the very large ratio between the length and the radius of the structure. Furthermore, by virtue of its frozen character, this copolymer structure is not sensitive to salinity or to changes in pH of the aqueous or organic medium that is to be made viscous.

By "shear thinning" is meant the diminution of the rheological (viscosity) properties under the effect of an increase in the stress, the shear, or the deformation that are applied to the system under study.

To this effect, the invention, according to a first aspect, provides filamentous polymer particles having a length/diameter ratio of more than 100, said particles being composed of block copolymers synthesized by controlled radical emulsion polymerization performed from at least one hydrophobic monomer in the presence of a water-soluble macroinitiator.

According to a first embodiment, said particles are synthesized from at least one hydrophobic monomer in the presence of a living macroinitiator derived from a nitroxide.

Said filamentous particles arc characteristically obtained in aqueous medium from synthesis of said block copolymers performed by heating the reaction mixture at a temperature of 60 to 120° C., with a percentage of the molar mass of the hydrophilic macroinitiator in the final block copolymer of between 10% and 50%, the degree of conversion of the hydrophobic monomer being at least 50%. The initial pH of the aqueous medium may vary between 5 and 10. This direct technique for preparing filamentous particles does not require the use of organic cosolvent.

A "living macroinitiator" is a polymer comprising at least one end suitable for reengagement in a polymerization reaction by addition of monomers at appropriate temperature and appropriate pressure. Said macroinitiator is advantageously prepared by CRP. A "water-soluble macroinitiator" is a polymer which is soluble in water and comprises at its end a reactive function capable of reinitiating a radical polymerization. This macroinitiator is composed principally of hydrophilic monomers, these being monomers having one or more functions capable of establishing hydrogen bonds with water. In the case of the polymerization of a hydrophobic monomer, an amphiphilic copolymer will be formed, with a hydrophilic block composed of the macroinitiator, while the hydrophobic block will be obtained from the polymerization of the hydrophobic monomer or monomers. According to one variant embodiment, said preformed water-soluble macroinitiator is added to the reaction medium comprising at least one hydrophobic monomer.

According to another variant within the first embodiment, said water-soluble macroinitiator is synthesized in the aqueous reaction medium in a preliminary step, without isolation of the macroinitiator formed and without removal of any residual hydrophilic monomers. This second variant is a "one-pot" polymerization.

The hydrophobic monomers may be selected from the following:
- vinylaromatic monomers such as styrene or substituted styrenes,
- alkyl, cycloalkyl, or aryl acrylates, such as methyl, ethyl, butyl, 2-ethylhexyl, or phenyl acrylate,
- alkyl, cycloalkyl, alkenyl, or aryl methacrylates such as methyl, butyl, lauryl, cyclohexyl, allyl, 2-ethylhexyl, or phenyl methacrylate,
- and vinylpyridine.

These hydrophobic monomers are added to the reaction medium which principally comprises water.

The percentage of the molar mass of the water-soluble macroinitiator in the final block copolymer is preferably between 10% and 30%.

Implementation of the method according to the invention produces filamentous polymer particles in which the mass fraction of the hydrophilic moiety constituting the block copolymer is less than 25%.

According to one embodiment, when the reaction medium is admixed with a crosslinking agent, crosslinked filamentous particles are obtained. Said crosslinking agent is a crosslinking comonomer other than the aforementioned hydrophobic monomers.

A crosslinking comonomer is a monomer which, by virtue of its reactivity with the other monomers present in the polymerization medium, is capable of generating a covalent three-dimensional network. From a chemical view point, a crosslinking comonomer generally comprises at least two polymerizable ethylenic functions which, by reacting, are capable of producing bridges between a number of polymer chains.

These crosslinking comonomers may be capable of reacting with the unsaturated hydrophobic monomers during the synthesis of said particles.

The crosslinking comonomers include divinylbenzenes, trivinylbenzenes, allyl (meth)acrylates, diallyl maleate polyol (meth)acrylates such as trimethylolpropane tri(meth)acrylates, alkylene glycol di(meth)acrylates which have from 2 to 10 carbon atoms in the carbon chain, such as ethylene glycol di(meth)acrylates, 1,4-butanediol di(meth)acrylates, and 1,6-hexanediol di(meth)acrylates, and N,N'-alkylenebisacrylamides, such as N,N'-methylenebisacrylamide. Preference will be given to using divinylbenzene or a dimethacrylate as crosslinking agent.

The filamentous particles according to the invention characteristically have a percentage of the molar mass of the hydrophilic macroinitiator in the final block copolymer of between 10% and 50%. As observed by TEM, these particles take the form of cylindrical fibers with a length/diameter ratio of more than 100; their diameter is constant over their whole length and is greater than or equal to 5 nm, while their length is greater than 500 nm, preferably greater than 1 micron, advantageously greater than 5 microns, and, more preferably still, is greater than or equal to 10 micrometers. The filamentous particles according to the invention maintain their form and structure in a dispersed medium, independently of their concentration in the medium and/or of changes in its pH or its salinity.

According to a second embodiment, said filamentous particles are synthesized by radical polymerization by reversible addition fragmentation transfer (RAFT) in water in the presence of a macromolecular RAFT agent (or RAFT macroagent) which is hydrophilic.

According to a second aspect, the invention pertains to a method for modifying the rheology of an aqueous or organic solution by means of said filamentous polymer particles. This method comprises a step of adding these filamentous particles to an aqueous or organic solution in a mass fraction of not less than 100 ppm, preferably from 500 to 10 000 ppm.

According to a further aspect, the invention is directed to a method for enhanced extraction of hydrocarbons by means of a polymeric additive, wherein said additive is mixed with water or brine in a proportion of at least 500 ppm of additive and then this mixture is injected under pressure into the rock; characteristically, said additive consists of the filamentous polymer particles according to the invention.

According to yet another aspect, the invention relates to a composition for modifying the rheology of an aqueous or organic solution intended more particularly for applications in cosmetology or paints, said composition comprising the filamentous polymer particles described above.

EXAMPLES

The invention will now he described with the aid of the examples below, which are given by way of illustration and not of limitation.

Example 1

Preparation of the Poly(Methacrylic Acid-co-sodium Styrenesulfonate) Macroinitiator Example 1 illustrates the preparation of a living poly(methacrylic acid-co-sodium styrenesulfonate) copolymer, used as macroinitiator, control agent, and stabilizer for the implementation of the method of the invention.

To this end, a mixture containing 75.2 g of methacrylic acid (2.0 mol.L$^{-1}$), 17.32 g of sodium styrenesulfonate (0.18 mol.L$^{-1}$ or $f_{0,SS}$=0.087) and 398 g of DMSO is degassed at room temperature by sparging with nitrogen. Then 3.782 g ($2.27\times10^{-2}$ mol.L$^{-1}$) of the alkoxyamine BlocBuilder®-MA (N-(2-methylpropyl)-N-(1-diethylphosphono-2,2-dimethyl-propyl)-O-(2-catboxylprop-2-yl)-hydroxylamine) are added.

Diagram of the BlocBuilder®-MA initiator.

Degassing is continued for 10 minutes. The degassed mixture is introduced into a 1 L three-neck flask preheated to 75° C. and surmounted by a condenser equipped with sparger, a nitrogen inlet, and a thermometer. Polymerization is performed at 76° C. and the time t is set to 0 when the temperature reaches 35° C. in the reaction mixture, The resulting macroinitiator is F(MAA-co-SS)-SG$_1$. Manipulation is halted after 16 minutes of reaction, by immersing the mixture with stirring, in a conical flask cooled with an ice bath. The reaction mixture is subsequently precipitated dropwise, in two stages, in a total volume of 4.5 liters of cooled dichloromethane subject to vigorous stirring. A white precipitate appears in the mixture. The mixture is filtered on a grade 4 porosity fit and then dried for 3 days under vacuum.

Samples are taken at the beginning and end times for the purpose of:
  determining the polymerization kinetics (determining the molar conversion and mass conversion by $^1$H NMR (DMSO d$_6$, 300 MHz);
  monitor the change in the number-average molar masses (M$_n$) as a function of the monomer conversion.

Table 1 below presents the characteristics of the purified macroinitiator

TABLE 1

| Time (min) | Conversion (%) | M$_n$,[a] Experimental (g · mol$^{-1}$) | M$_n$,[b] Theoretical (g · mol$^{-1}$) | I$_p$ | M$_n$,[c] Experimental (g · mol$^{-1}$) |
|---|---|---|---|---|---|
| 16 | 10 | 7200 | 1300 | 1.5 | 6350 |

[a] Determined by size exclusion chromatography in DMF with 1 g · L$^{-1}$ of LiBr, with calibration using polymethyl methacrylate, following purification and methylation of the methacrylic acid units to methyl methacrylate units;
[b] Calculated on the basis of methyl methacrylate units;
[c] Calculated on the basis of methacrylic acid units.

The experimental M$_n$ is determined by size exclusion chromatography in DMF containing 1 g/L of LiBr, with calibration using polymethyl methacrylate, following methylation of the methacrylic acid units to methyl methacrylate units. The flow rate is 0.8 mL/min with toluene as flow rate marker. The samples are prepared at a concentration of 5 mg/mL, are filtered on 0.45 μm filters, and are analyzed on Polymer Standards Service columns (Gram from 30-1000 Å). The polydispersity index I$_p$ is calculated on the basis of methyl methacrylate units.

The living nature of this macroinitiator is tested in a first phase by $^{31}$P NMR analysis, This characterization technique shows the presence of the phosphorous in the purified polymer.

A second, chain extension experiment is carried out in order to obtain a poly(methacrylic acid-co-sodium styrenesulfonate)-b-poly(styrene) block copolymer.

A mixture containing 61.4 mg of the above macroinitiator P(MMA-co-SS)-SG1 ($3.08\times10^{-3}$ mol.L$^{-1}$), 1.314 g of styrene (3.22 mol.L$^{-1}$), and 2.7335 g of DMSO is degassed at room temperature by sparging with nitrogen for 20 minutes in a 10 mL round-bottom flask. The flask is immersed in an oil bath at 120° C. for 5.5 hours.

The resulting polymer is analyzed to:
  determine the conversion of the polymerization (determined by gravimetry);
  monitor the value of the number-average molar mass (M$_n$) as a function of monomer conversion.

Table 2 below presents the characteristics of the P(MAA-co-SS)-b-P(Sty) polymer synthesized.

TABLE 2

| Time (h) | Conversion (%) | M$_n$, Experimental (g · mol$^{-1}$) | M$_n$, Theoretical (g · mol$^{-1}$) | I$_p$ |
|---|---|---|---|---|
| 5.5 | 38 | 58 350 | 65 750 | 1.44 |

The experimental M$_n$ is determined by size exclusion chromatography in DMF containing 1 g.L$^{-1}$ of LiBr, with calibration using polymethyl methacrylate, following methylation of the methacrylic acid units to methyl methacrylate units.

Comparative Example 2

Method for Obtaining Spherical Micelles

Example 2 illustrates the synthesis of particles in forms of spherical micelles of poly(sodium methacrylate-co-sodium styrenesulfonate)-b-poly(methyl methacrylate-co-styrene) block copolymers from the macroinitiator prepared and isolated in example 1.

A 250 mL single-neck round-bottom flask is charged with 41.5 g of deionized water, 4.1 g of P(MAA-co-SS)-SG$_1$ macroinitiator ($8.14\times10^{-3}$ mol.L$^{-1}$$_{water}$) prepared in example 1, 37.8 g of 1 M aqueous sodium hydroxide (1 equivalent relative to the methacrylic acid units), and 0.29 g of Na$_2$CO$_3$ ($3.46\times10^{-2}$ mol.L$^{-1}$). This mixture is stirred at room temperature, for approximately 15 minutes, until dissolution of the macroinitiator is complete, the latter then being in the poly(sodium methacrylate-co-sodium styrenesulfonate) form. Then 18.2 g of methyl methacrylate and 1.9 g of styrene are added (solids content=19.2%) and the mixture is degassed by sparging with nitrogen at room temperature for 30 minutes.

The mixture is introduced into a hot reactor under a pressure of 3 bar of nitrogen and with stirring at 250 rpm. The time t is set to 0 at 60° C. and the reactor is held at 90° C. throughout the polymerization. Samples are taken at regular intervals in order:
  to determine the kinetics of polymerization by gravimetry (measurement of dry matter);
  to monitor the change in number-average molar masses (M$_n$) with monomer conversion;
  to evaluate the colloidal characteristics of the latex (by Transmission Electron Microscopy (TEM) and by light scattering: average diameter of the particles, size distribution of the particles (polydispersity)).

Table 3 below presents the characteristics of the sampled latexes. The latex obtained at the end of polymerization is transparent and of very low viscosity. The appearance of the particles is analyzed by transmission electron microscopy. This microscope is a JEOL 100 Cx II microscope at 100 keV, equipped with an SIS Keen View high-resolution CCD camera. The image obtained is shown in appended FIG. 1 (67.2% conversion by mass, with a hydrophilic fraction of 23.4% by weight).

TABLE 3

| Time (h) | Conversion (%) | $M_n$, exp[a] g·mol$^{-1}$ | $M_n$, theo[b] g·mol$^{-1}$ | $I_p$[a] | pH | Dz[c] (nm) | Σ[d] |
|---|---|---|---|---|---|---|---|
| 0.25 | 17.6 | 19 700 | 12 700 | 1.27 | — | — | — |
| 0.5 | 26.9 | 23 150 | 15 570 | 1.37 | 7 | — | — |
| 0.75 | 37.6 | 31 700 | 18 900 | 1.2 | — | — | — |
| 1 | 56.2 | 35 960 | 24 700 | 1.23 | — | — | — |
| 2.9 | 67.2 | 40 500 | 28 000 | 1.29 | 6.85 | 36.8 | 0.16 |

[a]Determined by size exclusion chromatography in DMF with 1 g.L$^{-1}$ of LiBr, with calibration using polymethyl methacrylate, following methylation of the methacrylic acid units to methyl methacrylate units;
[b]Calculated on the basis of methyl methacrylate units;
[c]Intensity average diameter of the particles;
[d]Polydispersity of the latexes.

Example 3

Method for Obtaining Filamentous Particles According to the Invention

Example 3 illustrates the synthesis of filamentous particles of poly(sodium methacrylate-co-sodium styrenesulfonate)-b-poly(methyl methacrylate-co-styrene) block copolymers from the macroinitiator prepared and purified in example 1.

A 250 ml, single-neck round-bottom flask is charged with 55.7 g of deionized water, 2.29 g of P(MAA-co-SS)-SG$_1$ macroinitiator (4.54×10$^{-3}$ mol.L$^{-1}_{water}$) prepared in example 1, 23.7 g of 1M aqueous sodium hydroxide (1 equivalent relative to the methacrylic acid units), and 0.295 g of Na$_2$CO$_3$ (3.5×10$^{-2}$ mol.L$^{-1}$). This mixture is stirred at room temperature, for approximately 15 minutes, until. dissolution of the macroinitiator is complete, the latter then being in the poly (sodium methacrylate-co-sodium styrenesulfonate) form. Then 18.2. g of methyl methacrylate and 1.8 g of styrene are added (solids content=19.5%) and the mixture is degassed by sparging with nitrogen at room temperature for 30 minutes.

The mixture is then introduced into a Parr® reactor, series 5100, equipped with a 300 mL single-jacket glass tank with an internal diameter of 63 mm and a useful height of 102 mm. Stirring is maintained by a magnetic-drive stirrer fitted with a turbine, at 250 rpm. The tank of the reactor is heated beforehand.

The mixture is introduced into the hot reactor under a pressure of 3 bar of nitrogen and the time t is set at 0 at 60° C. and is maintained at 90° C. throughout the polymerization. Samples are taken at regular intervals in order:
- to determine the kinetics of polymerization by gravimetry (measurement of dry matter);
- to monitor the change in the number-average molar masses ($M_n$) with monomer conversion;
- to evaluate the colloidal characteristics of the latex (by TEM). Table 4 below presents the characteristics of the sampled latexes,

TABLE 4

| Time (h) | Conversion (%) | $M_n$, exp[a] g·mol$^{-1}$ | $M_n$, theo[b] g·mol$^{-1}$ | $I_p$[a] | pH |
|---|---|---|---|---|---|
| 0.25 | 18 | 23 900 | 17 200 | 1.3 | 7.9 |
| 0.5 | 25.5 | 31 600 | 21 350 | 1.24 | — |
| 0.75 | 43.6 | 42 850 | 31 400 | 1.13 | 7.55 |
| 1 | 52 | 46 700 | 36 000 | 1.13 | — |
| 3.1 | 68 | 53 700 | 44 900 | 1.2 | 6.7 |

[a]Determined by size exclusion chromatography in DMF with 1 g·L$^{-1}$ of LiBr, followed with calibration using polymethyl methacrylate, following methylation of the methacrylic acid units to methyl methacrylate units;
[b]Calculated on the basis of methyl methacrylate units.

The latex obtained at the end of polymerization is white and highly viscous.

Figure 2:
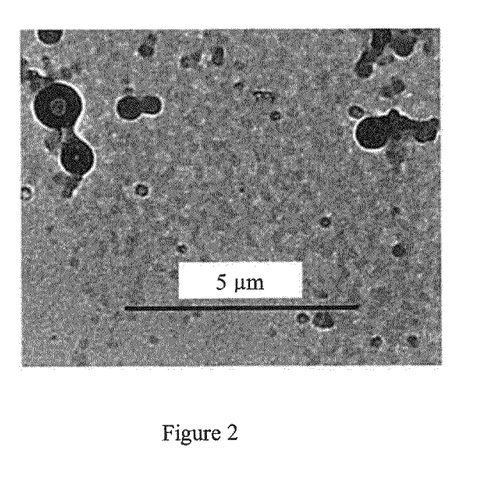
FIG. 2 corresponds to the TEM image of filamentous particles according to the invention, for a degree of conversion by mass of 25.5% and a proportion of hydrophilic fraction of 31% by weight.
Figure 3:
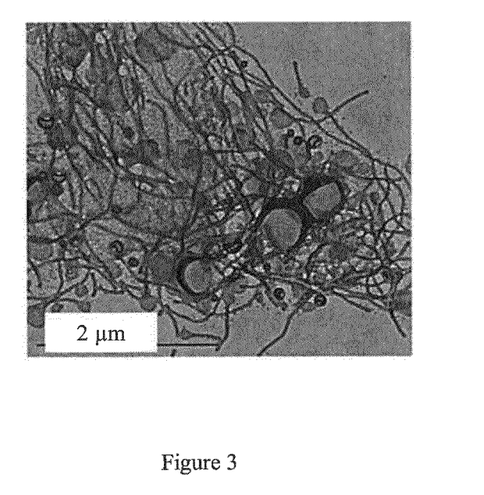
FIG. 3 corresponds to the TEM image of filamentous particles according to the invention, for a degree of conversion by mass of 52% and a proportion of hydrophilic fraction of 18% by weight.
Figure 4:
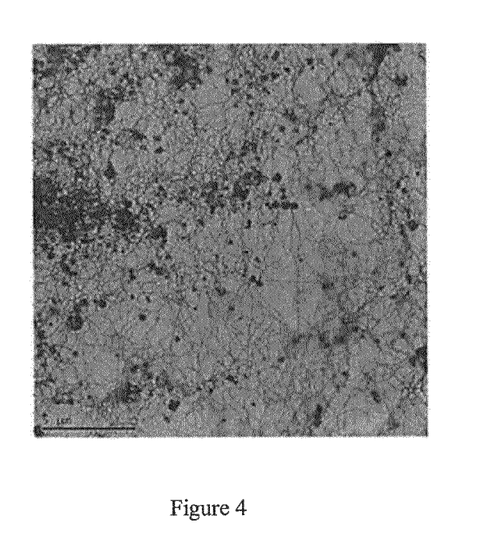
FIG. 4 corresponds to the TEM image of filamentous particles according to the invention, for a degree of conversion by mass of 68% and a proportion of hydrophilic fraction of 14.4% by weight.
Figure 5:
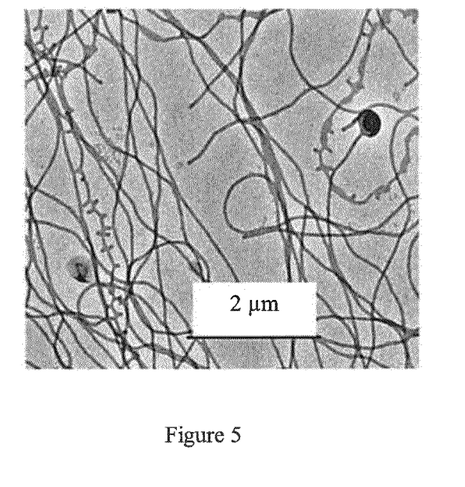
FIG. 5 illustrates the crosslinked filamentous particles according to the invention, for a degree of conversion by mass of 68% and a proportion of hydrophilic fraction of 14.4% by weight, as observed in TEM.

The appearance of the particles is analyzed by transmission electron microscopy (TEM). This microscope is a JEOL 100 Cx II microscope at 100 keV, equipped with an SIS Keen View high-resolution CCD camera. The images obtained are shown in FIGS. 2, 3, and 4, as indicated below:
- FIG. 2 corresponds to 25.5% conversion by mass, with a hydrophilic fraction of 31% by weight;
- FIG. 3 corresponds to 52% conversion by mass, with a hydrophilic fraction of 18% by weight;
- FIG. 4 corresponds to 68% conversion by mass, with a hydrophilic fraction of 14.4% by weight.

Comparative Example 4

Method for obtaining Filamentous Particles of "Pockets" Type

Example 4 illustrates the synthesis of hairlike nanoparticles in the form of 'pockets' of poly(sodium methacrylate-cc-sodium styrenesulfonate)-b-poly(methyl methacrylate-co-styrene) block copolymers from the macroinitiator prepared and purified in example 1.

A 250 mL single-neck round-bottom flask is charged with 65.8 g of deionized water, 1.1765 g of P(MAA-co-SS)-SG$_1$ macroinitiator (2.33×10$^{-3}$ mol.L$^{-1}_{water}$) prepared in example 1, 13.7 g of 1M aqueous sodium hydroxide (1 equivalent relative to the methacrylic acid units), and 0.299 g of Na$_2$CO$_3$ (3.54×10$^{-2}$ mol.L$^{-1}$). This mixture is stirred at room temperature, for approximately 15 minutes, until dissolution of the macroinitiator is complete, the latter then being in the poly (sodium methacrylate-co-sodium styrenesulfonate) form. Then 18.1 g of methyl methacrylate and 1.9 g of styrene are added (solids content=19.75%) and the mixture is degassed by sparging with nitrogen at room temperature for 30 minutes.

The mixture is introduced into a hot reactor (same configuration as in example 2) under a pressure of 3 bar of nitrogen and with stirring at 250 rpm. The time t is set to 0 at 60° C. and the reactor is maintained at 90° C. throughout the polymerization. Samples are taken at regular intervals in order:
- to determine the kinetics of polymerization by gravimetry (measurement of dry matter);
- to monitor the change in the number-average molar masses ($M_n$) with monomer conversion;
- to evaluate the colloidal characteristics of the latex (by transmission electron microscopy).

Table 5 below presents the characteristics of the sampled latexes.

TABLE 5

| Time (h) | Conversion (%) | $M_n$, exp[a] g·mol$^{-1}$ | $M_n$, theo[b] g·mol$^{-1}$ | $I_p$[a] | pH |
|---|---|---|---|---|---|
| 0.25 | 10.2 | 29 350 | 18 200 | 1.23 | 6.7 |
| 0.56 | 21.4 | 60 000 | 30 300 | 1.24 | — |

TABLE 5-continued

| Time (h) | Conversion (%) | $M_n$, exp[a] g·mol$^{-1}$ | $M_n$, theo[b] g·mol$^{-1}$ | $I_p$[a] | pH |
|---|---|---|---|---|---|
| 1 | 41.3 | 78 860 | 51 800 | 1.2 | — |
| 3.1 | 53.4 | 80 700 | 64 850 | 1.2 | 6.6 |

[a] Determined by size exclusion chromatography in DMF with 1 g·L$^{-1}$ of LiBr, followed with calibration using polymethyl methacrylate, following methylation of the methacrylic acid units to methyl methacrylate units;
[b] Calculated on the basis of methyl methacrylate units.

Figure 6:
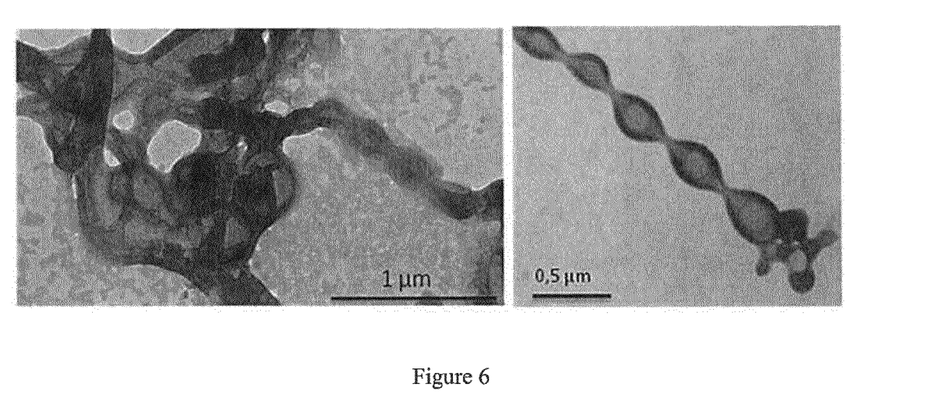
FIG. 6 corresponds to the TEM images of filamentous particles in "pocket" form, obtained with a poly(sodium methacrylate-co-sodium styrenesulfonate)-b-poly(methyl methacrylate-co-styrene)eopolymer.

The latex obtained at the end of polymerization is white and slightly viscous. The appearance of the particles is analyzed by TEM. This microscope is a JEOL 100 Cx II microscope at 100 keV, equipped with an SIS Keen View high-resolution CCD camera. The images obtained are presented in FIG. 6 and correspond to 53.4% conversion by mass with a hydrophilic fraction of 10% by weight.

Inventive Example 5

Method for Obtaining Crosslinked Filamentous Particles

Example 5 illustrates the synthesis of filamentous particles containing crosslinker, of poly(sodium methacrylate-co-sodium styrenesulfonate)-b-poly(methyl methacrylate-co-styrene-co-divinylbenzene) block copolymers from the macroinitiator prepared in example 1, A 250 mL single-neck round-bottom flask is charged with 57 g of deionized water, 2.63 g of P(MAA-co-SS)-SG$_1$ macroinitiator ($5.22 \times 10^{-3}$ mol.L$^{-1}_{water}$) prepared in example 1, 24.2 g of 1M aqueous sodium hydroxide (1 equivalent relative to the methacrylic acid units), and 0.296 g of Na$_2$CO$_3$ ($3.45 \times 10^{-2}$ mol.L$^{-1}$). This mixture is stirred at room temperature, for approximately 15 minutes, until dissolution of the macroinitiator is complete, the latter then being in the poly(sodium methacrylate-co-sodium styrenesulfonate) form. Then 18.1 g of methyl methacrylate and 0.784 g of styrene ($f_{0,Sty}$=0.04 mol; $f_{0,Sty}=n_{Sty}/(n_{Sty}+n_{MMA})$) are added and the mixture is degassed by sparging with nitrogen at room temperature for 30 minutes.

The mixture is introduced into a hot reactor (same configuration as in example 2) under a pressure of 3 bar of nitrogen and with stirring at 250 rpm. The time t is set to 0 at 60° C. and the reactor is maintained at 90° C. throughout the polymerization. After 50 minutes, 0.982 g of divinylbenzene ($f_{0,DVP}$=0.04 mol) ($f_{0,DVP}=n_{DVP}/(n_{DVP}+n_{MMA})$)(solids content=19%) is introduced into the mixture to crosslink the fibers after they have been formed.

Samples are taken at regular intervals in order:
to determine the kinetics of polymerization by gravimetry (measurement of dry matter);
to monitor the change in the number-average molar masses ($M_n$) with monomer conversion.

Table 6 below presents the characteristics of the sampled latexes.

TABLE 6

| Time (h) | Conversion (%) | $M_n$, exp[a] g·mol$^{-1}$ | $M_n$, theo[b] g·mol$^{-1}$ | $I_p$[a] | pH |
|---|---|---|---|---|---|
| 0.25 | 19 | — | 15 700 | — | 7.8 |
| 0.5 | 26 | — | 18 800 | — | — |
| 0.75 | 45 | — | 27 300 | — | — |
| 1 | 52 | — | 31 600 | — | — |
| 3 | 65 | — | 37 700 | — | — |

[a] Determined by size exclusion chromatography in DMF with 1 g·L$^{-1}$ of LiBr, with calibration using polymethyl methacrylate, following methylation of the methacrylic acid units to methyl methacrylate units;
[b] Calculated on the basis of methyl methacrylate units.

The latex obtained at the end of polymerization is in the form of a gel. The crosslinker is added during polymerization in order to allow the self-assembly of the particles prior to crosslinking the micelles in forms of elongated micelles.

Figure 7:
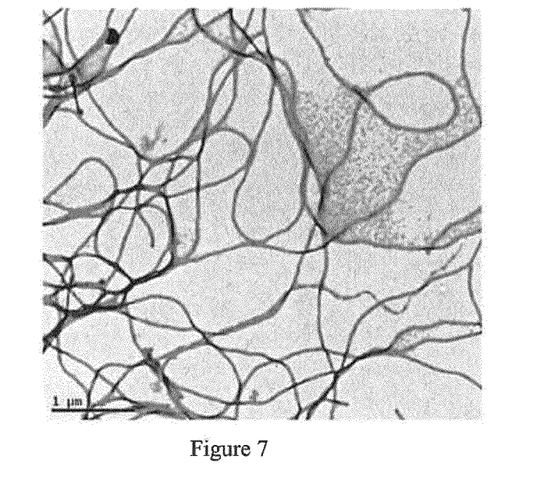
FIG. 7 corresponds to the TEM image of filamentous particles prepared in a 0.2% by weight solution and dialyzed for 4 days against ultrapure water.

The images obtained are presented in FIG. 7 which corresponds to 68% conversion by mass with a hydrophilic fraction of 14.4% by weight.

Example 6

Study of the Behavior of the Filamentous Particles According to the Invention in Dispersed Medium, with Variation of pH and Salinity Filamentous particles prepared in an aqueous solution at 0.2% by weight are dialyzed for 4 days against ultrapure water. FIG. 7 corresponds to the TEM image of dialyzed filamentous particles.

Figure 8:
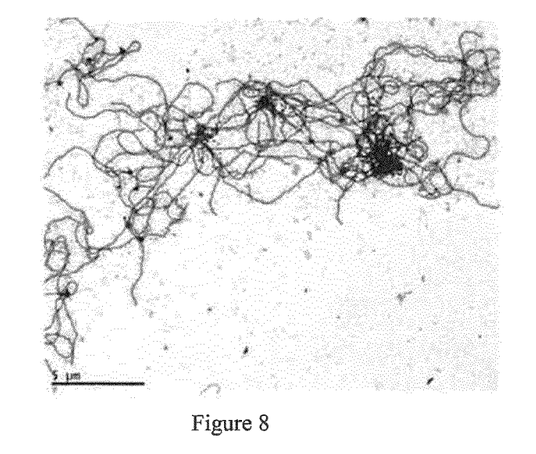
FIG. 8 corresponds to the TEM image of these filamentous particles after centrifuging.

Filamentous particles prepared in an aqueous solution at 0.2% by weight are centrifuged for 1 hour at 2100 rpm and at 10° C. The sediment (or centrifuging pellet) obtained is diluted in an aqueous solution. FIG. 8 corresponds to the TEM image of these particles after centrifuging.

Figure 9:
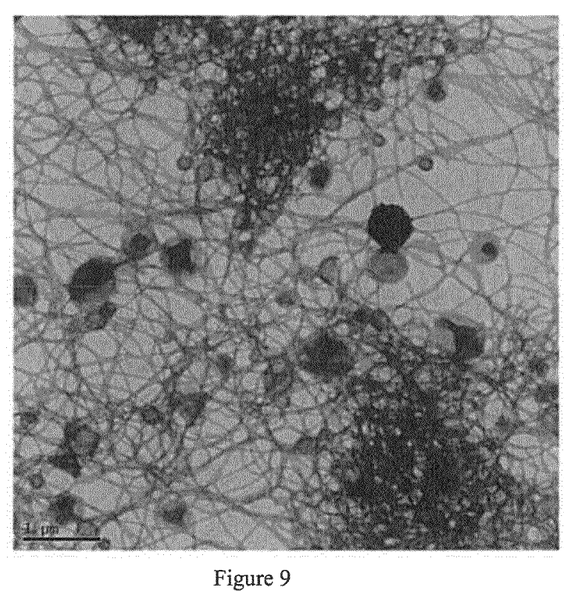
FIG. 9 corresponds to the TEM image of filamentous particles diluted in a solution at pH 5.
Figure 10:
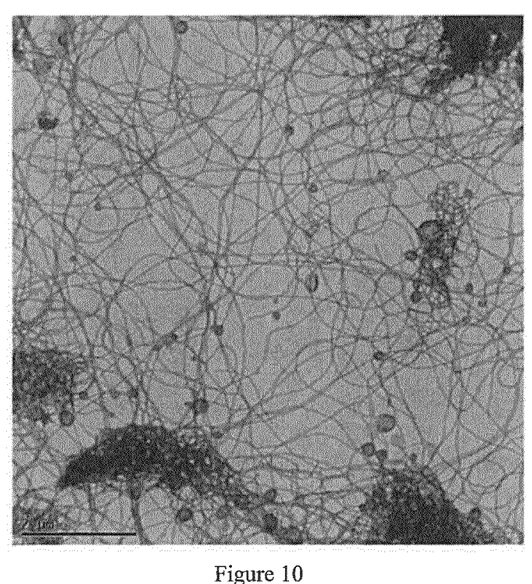
FIG. 10 corresponds to the TEM image of filamentous particles diluted in an aqueous solution containing 35 g of salt (NaCl) per 1 kg of water.

FIG. 9 corresponds to the TEM image of filamentous particles diluted in a solution at pH 5.

FIG. 10 corresponds to the TEM image of filamentous particles diluted in an aqueous solution containing 35 grams of salt (NaCl) per 1 kg of water.

These results show that the filamentous particles according to the invention maintain their shape and structure in dispersed medium, independently of their concentration in the medium, of the dialysis of the particles (FIG. 7), of the centrifuging of the mixture (FIG. 8) and/or of variations in its pH (FIG. 9) or its salinity (FIG. 10).

Example 7

Study of the Rheological Properties of the Filamentous Particles According to the Invention The rheological properties are measured using an Anton-Paar MCR301 imposed-stress rheometer. The measurements of flow (viscosity as a function of shear rate) are performed at room temperature (25° C.) with a Couette or plane/plane geometry (depending on the viscosity range). The example describes the rheological and shear-thinning properties endowed by the elongated fibrillar micelles in comparison with conventional micelle structures such as spheres or vesicles (or pockets). The details of these structures, in the form of transmission microscopy photos, are given in the table below:

The viscosity values are presented in table 7 below. The behavior is Newtonian when the viscosity is independent of shear rate. In the case of the shear-thinning behavior, the viscosity decreases with the increase in the shear rate.

These results show the difference in rheological behavior depending on the structure of the polymer particles: the spherical micelles (example 2) and the "pockets" (example 4) are dispersed without percolation in the medium, and exhibit Newtonian behavior and a small influence on the viscosity. The filamentous polymer particles according to the invention (final latex of example 3) exhibit a viscoelastic-solid behavior (at 19.6%), where the other morphologies give a liquid behavior. This behavior is due to a "percolation" of these long micelles and gives rise, even at low concentrations (3 and 2 g.L$^{-1}$), to a shear-thinning solution behavior. This behavior is maintained even after redilution of the centrifuged particles.

TABLE 7

| Sample | Rheological behavior | η at 10$^{-1}$ s$^{-1}$ mPa · s | η at 10 s$^{-1}$ mPa · s |
|---|---|---|---|
| Crude final latex of example 3 (fibers) Solids content = 19.6% | shear-thinning | 870 000 | 23 000 |
| Final latex of example 3 diluted in distilled water concentration = 3 g/L$^{-1}$ | shear-thinning | 160 | 4 |
| Final latex of example 3 diluted in distilled water concentration = 2 g/L$^{-1}$ | shear-thinning | 50 | 2 |
| Crude final latex of example 2 (spheres) Solids content = 19.6% | newtonian | 8 | 7 |
| Final latex of example 2 diluted in distilled water concentration = 2 g/L$^{-1}$ | newtonian | 4 | 2 |
| Crude final latex of example 4 (pockets) Solids content = 19.6% | newtonian | 2.3 | 2 |
| Final latex of example 4 diluted in distilled water concentration = 2 g/L$^{-1}$ | newtonian | 1.5 | 1.5 |
| Distilled water | newtonian | 1 | 1 |

Abbreviations:
 CRP—controlled radical polymerization
 P4VP—poly(4-vinylpyridine)
 PNaA—poly(sodium acrylate)
 SG1—N-tert-butyl-N-[1-diethylphosphono(2,2-dimethylpropyl)]
 S or Sty—styrene
 SS—sodium styrenesulfonate
 AA—acrylic acid
 PEGA—poly(ethylene glycol) methyl ether acrylate
 TEM—transmission electron microscopy
 RAFT—polymerization by addition fragmentation (Reversible Addition Fragmentation chain Transfer)
 MAA—methacrylic acid
 DMSO—dimethyl sulfoxide
 DMF—dimethylformamide
 rpm—revolutions per minute
 $f_{0,sty}$—initial molar fraction of styrene in the mixture of monomers
 $f_{0,SS}$—initial molar fraction of sodium sulfonate in the mixture of monomers
 $f_{0,DVP}$—initial molar fraction of divinylbenzene in the mixture of monomers
 BlocBuilder®-MA—(N-(2-methylpropyl)-N-(1-diethylphosphono-2,2-dimethylpropyl)-O-(2-carboxylprop-2-yl) hydroxylamine

The invention claimed is:

1. A filamentous polymer particle having a length/diameter ratio of more than 100 and composed of block copolymers synthesized by controlled radical emulsion polymerization.

2. The particle as claimed in claim 1, wherein said particle is synthesized from at least one hydrophobic monomer in the presence of a living macroinitiator derived from a nitroxide, and wherein:
 said filamentous particle is obtained in aqueous medium during the synthesis of said block copolymers, formed by heating the reaction medium at a temperature of 60 to 120° C.,
 said macroinitiator is water-soluble,
 the percentage of the molar mass of the water-soluble macroinitiator in the final block copolymer is between 10% and 50%, and in that
 the degree of conversion of the hydrophobic monomer is at least 50%.

3. The particle as claimed in claim 1, having a length of more than 500 nm, more than 1 micron, or more than 5 microns.

4. The particle as claimed in claim 2, wherein the hydrophobic monomer is selected from the group consisting of vinylaromatic monomers alkyl, cycloalkyl, or aryl acrylates; alkyl, cycloalkyl, alkenyl or aryl methacrylates, and vinylpyridine.

5. The particle as claimed in claim 2, wherein the percentage of the molar mass of the water-soluble macroinitiator in the final block copolymer is between 10% and 30%.

6. The particle as claimed in claim 2, wherein the mass fraction of the hydrophilic moiety constituting the final block copolymer is less than 25%.

7. The particle as claimed in claim 2, further comprising a crosslinking comonomer.

8. The particle as claimed in claim 7, wherein the crosslinking comonomer is selected from the group consisting of divinylbenzenes, trivinylbenzenes, allyl (meth)acrylates, diallyl maleate polyol (meth)acrylates, and alkylene glycol di(meth) acrylates which have from 2 to 10 carbon atoms in the carbon chain.

9. The particle as claimed in claim 1, wherein said particle is synthesized by radical polymerization by reversible addition fragmentation transfer (RAFT) in water from at least one hydrophobic monomer in the presence of a macromolecular RAFT agent (or RAFT macroagent) which is hydrophilic.

10. A method for modifying the rheology of an aqueous or organic solution comprising a step of adding one or more filamentous particles of claim 1 to an aqueous or organic solution in a mass fraction of not less than 100 ppm.

11. A method of enhanced hydrocarbon extraction by means of a polymeric additive, comprising the step of admixing said additive with water or brine in a proportion of at least 500 ppm of additive and then injecting said admixture under pressure into a rock, wherein said additive comprises the filamentous polymer particles defined in claim 1.

12. The method as claimed in claim 10 in the preparation of paints.

13. The method as claimed in claim 10 in the preparation of cosmetic products.

14. The particle of claim 4, wherein said vinylaromatic monomers are selected from the group consisting of styrene and substituted styrenes; said alkyl, cycloalkyl, or aryl acrylates are selected from the group consisting of methyl acrylate, ethyl acrylate, butyl acrylate, 2-ethylhexyl acrylate, and phenyl acrylate; and said alkyl, cycloalkyl, alkenyl, or aryl methacrylates are selected from the group consisting of methyl methacrylate, butyl methacrylate, lauryl methacrylate, cyclohexyl methacrylate, allyl methacrylate, 2-ethylhexyl methacrylate, and phenyl methacrylate.

15. The method of claim 10 comprising a step of adding one or more filamentous particles of claim 1 to an aqueous or organic solution in a mass fraction of 500 to 10 000 ppm.

* * * * *